(12) United States Patent
Dukoff (10) Patent No.: US 9,717,657 B2
(45) Date of Patent: Aug. 1, 2017

(54) COMPOSITION AND METHOD OF USING MEDICAMENT FOR ENDODONTIC IRRIGATION, STEM CELL PREPARATIONS AND TISSUE REGENERATION

(71) Applicant: Amy Dukoff, New York, NY (US)

(72) Inventor: Amy Dukoff, New York, NY (US)

(*) Notice: Subject to any disclaimer, the term of this patent is extended or adjusted under 35 U.S.C. 154(b) by 874 days.

(21) Appl. No.: 13/954,434

(22) Filed: Jul. 30, 2013

(65) Prior Publication Data

US 2014/0113254 A1    Apr. 24, 2014

Related U.S. Application Data

(60) Provisional application No. 61/717,691, filed on Oct. 24, 2012.

(51) Int. Cl.
*A61C 5/02* (2006.01)
*A61K 6/00* (2006.01)
*A61C 5/50* (2017.01)

(52) U.S. Cl.
CPC .............. *A61K 6/0035* (2013.01); *A61C 5/50* (2017.02); *A61K 6/0041* (2013.01)

(58) Field of Classification Search
CPC .. A61C 5/04; A61C 5/02; A61K 6/00–6/0067
USPC ............. 433/224, 81, 216, 226; 424/693, 49
See application file for complete search history.

(56) References Cited

U.S. PATENT DOCUMENTS

| | | |
|---|---|---|
| 2,487,558 A | 11/1949 | Kamlet |
| 3,087,839 A | 4/1963 | Hamilton |
| 3,134,641 A | 5/1964 | Gleichert |
| 3,563,694 A | 2/1971 | Minton |
| 3,572,989 A | 3/1971 | Tatara et al. |
| 3,950,499 A | 4/1976 | Miyashin et al. |
| 4,121,904 A | 10/1978 | Schamper |
| 4,248,848 A | 2/1981 | Murakami et al. |
| 4,352,678 A | 10/1982 | Jones et al. |

(Continued)

OTHER PUBLICATIONS

Rouse et al., "A review of keratin-based biomaterials for biomedical application," Materials 2010, 3, pp. 999-1014.

(Continued)

*Primary Examiner* — Yogesh Patel
(74) *Attorney, Agent, or Firm* — Thomas A. O'Rourke; Bodner & O'Rourke, LLP (57) ABSTRACT

A composition for endodontic irrigation is provided. The composition includes a chemical depilatory during intra-canal, and chemo-mechanical instrumentation in endodontic. The composition includes calcium hydroxide or potassium hydroxide, sodium hydroxide, and potassium thioglycolate or calcium thioglycolate to form an effective root canal medicament. Further, the composition may incorporate mineral oil, urea, cetearyl alcohol, D&C yellow No. 8, chromium hydroxide, theobroma cocoa seed butter, iron oxides, fragrances, and ceteareth-20 to enhance its functioning. The composition disinfects, lubricates, chelates, irrigants, dissolves, and facilitates removal of the pulpal tissue and debris. Furthermore, the composition reduces and even eliminates bacteria from micro-endodontic systems. Further, the composition of the present invention enhances eradicating pathogens along with chemo-mechanical debridement of the root canal system.

9 Claims, 7 Drawing Sheets

(56) References Cited

U.S. PATENT DOCUMENTS

| | | | |
|---|---|---|---|
| 4,845,845 A | 7/1989 | Scott | |
| 5,804,566 A | 9/1998 | Carson et al. | |
| 5,849,719 A | 12/1998 | Carson et al. | |
| 6,206,869 B1 | 3/2001 | Tapper | |
| 6,291,397 B1 | 9/2001 | Wilkins | |
| 6,425,891 B1 | 7/2002 | Tapper | |
| 6,708,531 B1 | 3/2004 | Thanikaivelan et al. | |
| 6,957,554 B2 | 10/2005 | Saravanabhavan et al. | |
| 7,022,005 B2 | 4/2006 | Potter et al. | |
| 7,238,342 B2 | 7/2007 | Torabinejad et al. | |
| 7,332,156 B2 | 2/2008 | Bowman et al. | |
| 7,476,466 B2 | 1/2009 | Izumi et al. | |
| 7,893,215 B2 | 2/2011 | Bowman et al. | |
| 8,002,544 B2 | 8/2011 | Rizoiu et al. | |
| 8,062,634 B2 | 11/2011 | Bowman et al. | |
| 2002/0058232 A1 | 5/2002 | Weiss et al. | |
| 2002/0146380 A1 | 10/2002 | Nambu et al. | |
| 2003/0118535 A1* | 6/2003 | Lustbader | A61K 8/06 424/70.1 |
| 2003/0203861 A1 | 10/2003 | Carson et al. | |
| 2004/0101809 A1 | 5/2004 | Weiss et al. | |
| 2005/0118115 A1 | 6/2005 | Fontenot | |
| 2007/0111915 A1 | 5/2007 | Ashworth et al. | |
| 2008/0138304 A1 | 6/2008 | Biggs et al. | |
| 2008/0193402 A1* | 8/2008 | Adamy | A61Q 9/04 424/70.1 |
| 2009/0005462 A1* | 1/2009 | Gunn | A61K 8/42 514/785 |
| 2009/0010858 A1 | 1/2009 | Asano | |
| 2009/0075229 A1 | 3/2009 | Rizoiu et al. | |
| 2009/0088476 A1 | 4/2009 | Pond et al. | |
| 2009/0285766 A1 | 11/2009 | Kishen et al. | |
| 2009/0304606 A1* | 12/2009 | Primus | A61K 8/365 424/49 |
| 2010/0215643 A1 | 8/2010 | Clevenger et al. | |
| 2011/0020765 A1 | 1/2011 | Maxwell et al. | |
| 2011/0054036 A1* | 3/2011 | Haapasalo | A61K 31/14 514/635 |
| 2011/0256495 A1* | 10/2011 | Mounir | A61O 5/02 433/1 |
| 2011/0302723 A1* | 12/2011 | Mansson | A61K 8/46 8/161 |
| 2013/0042421 A1* | 2/2013 | Smith | A61K 8/31 8/161 |

OTHER PUBLICATIONS

"Bone", http://en.wikipedia.org/wiki/Bone.
"Calcium hydroxide has limited effectiveness in eliminating bacteria from human root canal", http://www.nature.com/ebd/journal/v8/n1/full/6400467a.html, Evidence-Based Dentistry (2007) 8, 15-16.
"Cetearyl Alcohol NF", http://www.ingredientstodiefor.com/item/Cetearyl_Alcohol_NF_30_70_Blend_/150.
"Chemical Depilatory", http://en.wikipedia.org/wiki/Chemical_depilatory.
Kim et al., "Chemical interaction of alexidine and sodium hypochlorite," Journal of Endodontics 38, 112-6, 2012.
"Cleaning and Preserving Animal Skulls," The University of Arizona Cooperative Extension.
"Cysteine Cathepsins in Human Dentin-Pulp Complex", http://scienceindex.com/stories/495642/Cysteine_Cathepsins_in_Human_DentinPulp_Complex.html.
Gomez, "Dental Pulp Sensory Function. Pain.," E. J. E. R. Electronic Journal of Endodontics Rosario, Ano 2010, vol. 02, Oct. 2011.
"Dental Pulp Stem Cells", http://en.wikipedia.org/wiki/Dental_pulp_stem_cells.
Lindsay, "Discussion on Dental Structures and Dental Caries," section of odontology, Proceedings of the royal society of medicine, Apr. 8, 1946, vol. 637, Sectional p. 21.
Abd-Elmeguid et al., "Dentin matrix protein-1 activates dental pulp fibroblasts," J Endod. 2012;38(1):75-80.
"Disulfide Bond", http://en.wikipedia.org/wiki/Disulfide_bond.
Kara et al. "Effect of different final irrigation solutions on dentinal tubule penetration depth and percentage of root canal sealer," J Endod. Jun. 2012;38(6):860-3.
"Hair follicle", http://en.wikipedia.org/wiki/Hair_follicle.
"Hair Remover", http://www.madehow.com/Volume-4/Hair-Remover.html.
"How MSM Works to Improve Joint Health", http://www.msmguide.com/jointpain/improvejointhealth/.
Synthes, "Reamer/Irrigator/Aspirator (RIA) for intramedullary reaming and bone harvesting".
Dutner et al., "Irrigation trends among American Association of Endodontists members: a web-based survey," J Endod. 2012;38:37-40.
"Keratin", http://www.bio-medicine.org/biology-definition/Keratin/.
Yang et al. "Lipopolysaccharide-induced dental pulp cell apoptosis and the expression of Bax and Bcl-2 in vitro," Braz. J. Med. Biol. Res. 43, 1027-1033.
Spectrum chemicals and laboratory products, "Material Safety Data Sheet—Potassium Thioglycolate, 42 Percent Aqueous Solution," https://www.spectrumchemical.com/MSDS/P2105X.pdf.
Peng et al., "Mesenchymal stem cells and tooth engineering," Int J Oral Sci 1:6-12 doi:10.4248/ijos.08032 (2009).
"Mineral Oil", http://en.wikipedia.org/wiki/Mineral_oil.
Quah et al., "N-acetylcysteine inhibits growth and eradicates biofilm of Enterococcus faecalis," Journal of endodontia, 2011.
"Nair (hair removal)", http://en.wikipedia.org/wiki/Nair_%28hair_removal%29.
Shakhova et al., "Neural crest-derived stem cells," StemBook ed. The Stem Cell Research Community.
"Neurokeratin", http://dictionary.reference.com/browse/neurokeratin.
"Odontogenic Cyst", http://www.dent.ucla.edu/pic/visitors/Cysts/page1.html.
"Peripheral Nerves", http://vanat.cvm.umn.edu/neurLab1/nerves.html.
Kandaswamy et al., "Root canal irrigants" J Conserv Dent. 2010; 13:256-264.
Qin et al., "Smad 1/5 is involved in bone morphogenetic protein-2-induced odontoblastic differentiation in human dental pulp cells," J Endod. 2012; 38:66-71.
"Smear layer", http://en.wikipedia.org/wiki/Smear_layer.
"Sodium Hydroxide", http://en.wikipedia.org/wiki/Sodium_hydroxide.
"Sodium hypochlorite", http://en.wikipedia.org/wiki/Sodium_hypochlorite.
Gianluca et al., "Ultrasonics in endodontic surgery: a review of the literature," Ann Stomatol (Roma), Apr.-Jun. 2010; 1(2):6-10.
"What are the Ingredients in Nair", http://www.ehow.com/about_4571104_what-ingredients-nair.html.
"What's Inside: Nair Hair Remover, Feel the Burn!", http://www.wired.com/science/discoveries/magazine/16-01/st_nair.
"Why You Need Protein in Your Diet", http://www.dummies.com/how-to/content/why-you-need-protein-in-your-diet.html.
Yang et al., "Redox modification of cysteine residues regulates the cytokine activity of HMGB1," Molecular Medicine, vol. 18, No. 3, pp. 250-259, 2012.
Laboratory Testing Records, "Time Kill Study GLP Report," on file at IrriMax Corporation. 6. Denton, G. (2001).
"Lab evaluation of the Testing of the Present Invention".
"Slides from Amy Dukoff related to the present invention".
Carter-Wallace Inc., Trademark on "Nair", Filed on Jan. 25, 1990, Registered on Oct. 23, 1990.
Reckitt & Colman Ltd, Trademark on "Veet", Filed on Nov. 6, 2007, Registered on Jul. 29, 2008.
"Fax from Amy Dukoff related to Laboratory test results".
International Search Report & Written Opinion issued Jan. 16, 2014 in connection with corresponding International Application No. PCT/US2013/065825 (9 pages total).

* cited by examiner

COMPOSITION AND METHOD OF USING MEDICAMENT FOR ENDODONTIC IRRIGATION, STEM CELL PREPARATIONS AND TISSUE REGENERATION

CROSS-REFERENCE TO RELATED APPLICATIONS

This application claims the benefit of U.S. Provisional Application Ser. No. 61/717,691, filed Oct. 24, 2012, entitled "COMPOSITION AND METHOD OF USING MEDICAMENT FOR ENDODONTIC IRRIGATION, STEM CELL PREPARATIONS AND TISSUE REGENERATION," which is incorporated herein by reference in its entirety.

BACKGROUND

Field of the Invention

Embodiments of the present invention generally relate to a composition and a method for irrigating surfaces for dental and medical procedures and, in particular, to a composition and method of using medicament for endodontic irrigation, stem cell preparations, and tissue regeneration.

Description of Related Art

Root canal treatment is normally required whenever tissues in root canals are injured or infected. Bacteria destroys pulp (i.e., soft tissues occupying inner space of teeth) and can also leak out of root into surrounding bone. The root canal treatment is done by removing bacteria and organic matter from the root canal and then filling the space in order to prevent bacterial invasion and irritation to surrounding tissues.

In the root canal treatment (or endodontic), success of root canal therapy is dependent on a practitioner's ability to remove all tissue, debris and microorganisms from the root canal area. Treatment complication or failures may occur if infecting bacteria are not eliminated completely from the root canal space and/or the dentinal tubules. Bacterial invasion of microscopic spaces in dentin, irregularities or imperfections in the dentin structure including isthmuses, ramifications, accessory canals and apical deltas, can further complicate the root canal treatment and its outcome.

Currently, the practitioner uses many types of irrigants in order to chemo-mechanically prepare the root canal system for obturation. However, present endodontic irrigants require use of a combination of irrigants for chemo-mechanical instrumentation. Some endodontic irrigants are utilized for their tissue dissolving ability. For example, sodium hypochlorite is a widely used tissue dissolving agent. Sodium hypochlorite's effectiveness is dependent on its concentration and irrigation time and is highly effective at 5.25% for 40 minutes and ineffective at 1.3-2.5%. Further, antibacterial agents are either bactericidal or bacteriostatic. For example, chlorohexidine is bactericidal while a mixture of tetracycline, an acid, and a detergent (MTAD) is bacteriostatic. Furthermore, other endodontic irrigants are chelating agents like Ethylenediaminetetraacetic acid (EDTA) that remove the smear layer and decalcify dentin. However, as discussed above, the success of the root canal treatment is dependent on the practitioner's ability to remove all the contents from within the root canal system before obturation.

Pulp calcifications within the root canal system are obstructions to debridement in a variety of forms. Pulp stones are isolated areas of calcifications. While other calcifications take the form of diffuse calcification and irregular linear calcifications. Calcifications and calcification blockages present a problem to successfully negotiate the canal during instrumentation.

Conventional endodontic intra-canal medicaments have specific limitations. For example, sodium hydroxide's ability to eradicate all the bacteria in the root canal system is not possible. Sodium hydroxide needs to be in direct contact for it to be effective but this is difficult to attain. Sodium hydroxide cannot diffuse into direct contact when there are calcifications present that are natural obstructions.

As another example, sodium hypochlorite can dissolve organic tissue but cannot predictably inactivate endotoxins. Also, sodium hypochlorite loses its effectiveness when it is diluted. Furthermore, it is irritating to tissue.

Additionally, ethylenediaminetetraacetic acid (EDTA) is effective for removing inorganic material as a chelating agent. However, EDTA should not be used with sodium hypochlorite, as it reduces the available chloride making sodium hypochlorite not effective as an irrigant.

MTAD is a mixture of doxycycline, citric acid, and Tween 80 (a detergent) in order to remove some of the smear layer. However, it is not effective against fungi within the root canal system. Also, it can have a negative effect on the bond strength of root canal sealers when used as a final intra-canal rinse. Finally, chlorhexidine or chlorhexidine digluconate can be used for disinfection but cannot dissolve tissue.

Thus, there is a need for a composition and method for removing all tissue, debris and microorganisms and dislodging calcifications from the root canal system during root canal treatment and for preparing surfaces for stem cell therapy and for tissue regeneration.

SUMMARY

Embodiments in accordance with the present invention provide a composition for endodontic irrigation. The composition includes calcium hydroxide, sodium hydroxide, and potassium thioglycolate.

Embodiments in accordance with the present invention further provide a method for endodontic irrigation. The method includes irrigating a root canal with a composition comprising calcium hydroxide, sodium hydroxide, potassium thioglycolate, water, mineral oil, urea, cetearyl alcohol, and ceteth-20.

Embodiments in accordance with the present invention further provide a composition of matter for endodontic irrigation. The composition of matter includes calcium hydroxide, sodium hydroxide, potassium thioglycolate, water, mineral oil, urea, cetearyl alcohol, and ceteth-20.

Further, the present invention can provide a number of advantages. First, embodiments of the present invention provide a composition and a method for using a chemical depilatory for endodontic usages. The present invention utilizes ability of the chemical depilatory to break disulfide bonds in the tissues of pulpal area. By breaking the disulfide bonds, the chemical depilatory provides for weakening the structure of the pulpal tissue. Further, the present invention provides a composition that provides results at a faster pace. The chemical depilatories work at a fast rate of within five minutes. The chemical depilatory's ability to be effective within minutes of its application provides an advantage in patient care as patients can keep their mouth open for a limited time. Further, the composition and the method are capable of removing debris that is formed during dental procedure and dissolving proteins along with calcifications within the pulpal chamber. Furthermore, the present invention provides a composition that is also capable of bleaching teeth.

Further, the present invention provides integrating many processes to be effective at same time. The usage of the chemical depilatory in endodontic facilitates complete removal of pulpal debris as it lubricates, irrigates, disinfects, dissolves, cleanses and removes the smear layer. Further, the chemical depilatory has antimicrobial benefits. The present invention utilizes the chemical depilatory and provides a single irrigant that combines tissue dissolving ability and smear layer removal capacity with antibacterial properties. Further, the present invention facilitates breaking glycosaminoglycans (GAG) bond within the smear layer and facilitates its removal. Further, the present invention facilitates dislodging pulpal calcification by breaking the bonds in the tissue surrounding it.

Further, the present invention utilizes a chemical irrigant for removal of soft and connective tissue from within a hard bony cavity. The present invention utilizes a chemical depilatory for removing a soft tissue, necrotic tissue, debris, and calcified tissue from within the hard tissue cavity. Further, the present invention provides a composition that is effective on unprepared tooth surfaces as well as on prepared tooth surfaces. Furthermore, the composition, provided by the present invention, is useful in medicine, especially in long bones and in preparing skeletons for museums, etc.

These and other advantages will be apparent from the disclosure of the present invention contained herein.

The preceding is a simplified summary of the present invention to provide an understanding of some aspects of the present invention. This summary is neither an extensive nor exhaustive overview of the present invention and its various embodiments. It is intended neither to identify key or critical elements of the present invention nor to delineate the scope of the present invention but to present selected concepts of the present invention in a simplified form as an introduction to the more detailed description presented below. As will be appreciated, other embodiments of the present invention are possible, utilizing, alone or in combination, one or more of the features set forth above or described in detail below.

BRIEF DESCRIPTION OF THE DRAWINGS

The above and still further features and advantages of the present invention will become apparent upon consideration of the following detailed description of embodiments thereof, especially when taken in conjunction with the accompanying drawings, and wherein.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include," "including," and "includes" mean including but not limited to. To facilitate understanding, like reference numerals have been used, where possible, to designate like elements common to the figures.

DETAILED DESCRIPTION

The present invention will be illustrated below in conjunction with an exemplary application, e.g., root canal treatment. Although well suited for use with, e.g., a medical application having disulphide bonds and requiring breakage of disulphide bonds, the present invention is not limited to any particular type of medical application. Those skilled in the art will recognize the disclosed techniques may be used in any medical or non-medical application in which it is desirable to provide breakage of disulphide bonds.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

The terms "determine", "calculate" and "compute," and variations thereof, as used herein, are used interchangeably and include any type of methodology, process, mathematical operation or technique.

In the following detailed description, numerous specific details are set forth in order to provide a thorough understanding of embodiments or other examples described herein. In some instances, well-known methods, procedures, compositions, or components have not been described in detail, so as to not obscure the following description. Further, the examples disclosed are for exemplary purposes only and other examples may be employed in lieu of, or in combination with, the examples disclosed. It should also be noted the examples presented herein should not be construed as limiting of the scope of embodiments of the present invention, as other equally effective examples are possible and likely.

Figure 1:
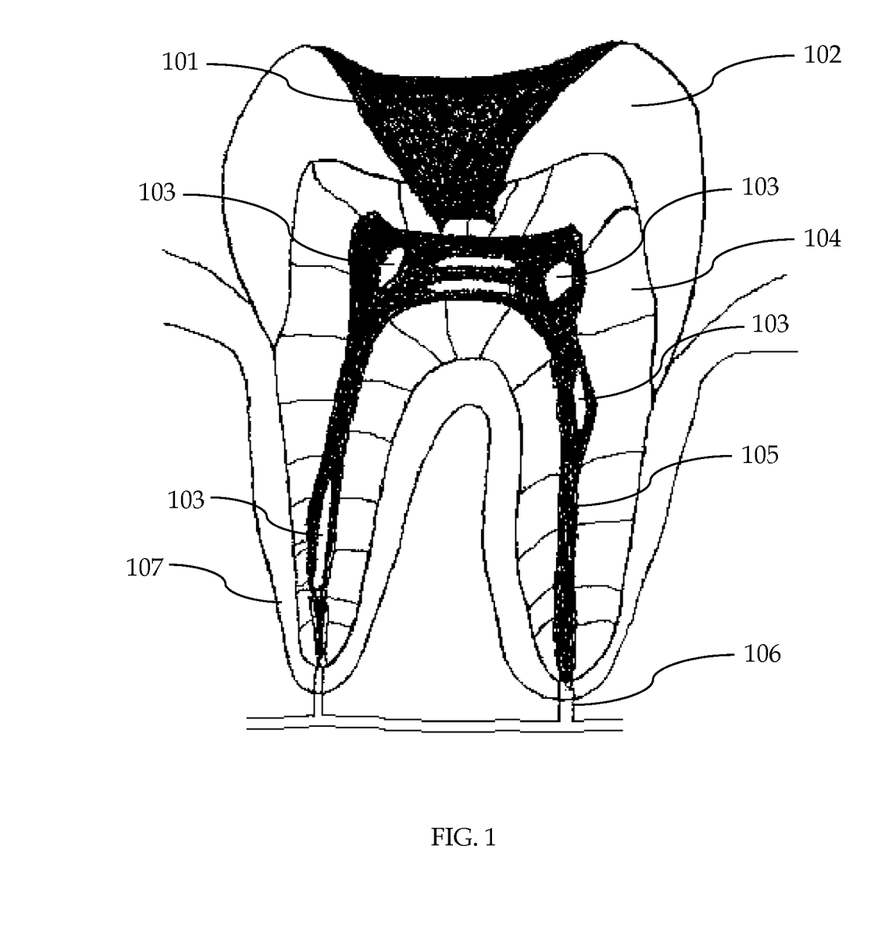
FIG. 1 is a cross sectional view of a tooth with tooth decay about to go under treatment in accordance with an embodiment of the present invention.

FIG. 1 shows a cross-sectional view of a tooth 100 in accordance with an embodiment of the present invention. The tooth 100 includes tooth decay 101, as shown in the figure. Because of the tooth decay 101, the tooth 100 is under a treatment (i.e., root canal treatment). The tooth 100 further includes enamel 102, a pulpal calcification 103, a dentin 104, and a pulp 105. The tooth 100 further includes an apex 106 and a periodontal ligament 107. The purpose of the root canal treatment is to completely remove the pulp 105 (as it is infected or injured, and can infect surrounding teeth), and that includes removal of all tissues, debris and microorganisms from root canal area.

Tissues of the pulp 105 differ from tissues of the enamel 102 and tissues of the dentin 104. Pulpal tissue is a highly vascular and soft tissue. On other hand, the dentin 104 and the enamel 102 are hard, calcified, and mineralized tissues. The enamel 102 and the dentin 104 include same type of inorganic materials, but differ in degree of calcification and mineralization of the inorganic material. Further, protein of the enamel 102 is resistant to enzymatic hydrolysis. The enamel 102 is more resistant to enzymatic digestion than skin. Therefore, the protein of the enamel 102 is not classified as a type of keratin and is not affected by actions of a chemical depilatory, if the chemical depilatory is applied. Further, chemical composition of the tissues of the pulp 105 is different than chemical composition of the dentin 104 and the enamel 102.

According to an embodiment of the present invention, the pulp 105 includes disulphide bonds. The disulphide bond is a covalent bond that is derived by coupling of two thiol groups. The linkage is called an SS bond or disulphide bridge. The disulphide bonds are present in a plurality of living and non-living species. For example, disulfide bonds are present in bacteria as they serve as a protective role for bacteria. Further, in humans also, disulfide bonds are found in secretory proteins, lysosomal proteins, and exoplasmic domains of stability of proteins in extracellar tissue. Further, disulfide bonds are also found in nuerokeratin of the myelinated sensory nerve A fibers. Furthermore, disulfide bonds are present in HNGB1 (high-mobility group protein-1), which is a mediator of inflammation. According to an embodiment of the present invention, a method is provided for utilizing the disulfide Bond or S—S bond for cleaning out the pulp 105.

Tissues of the pulp 105 include disulfide bonds. Disulfide bonds acts like a glue and hold together molecules and proteins. If the disulfide bonds are broken, it may weaken and break down structure of the pulp 105 and facilitate removal of tissues from the pulp 105.

Figure 2:
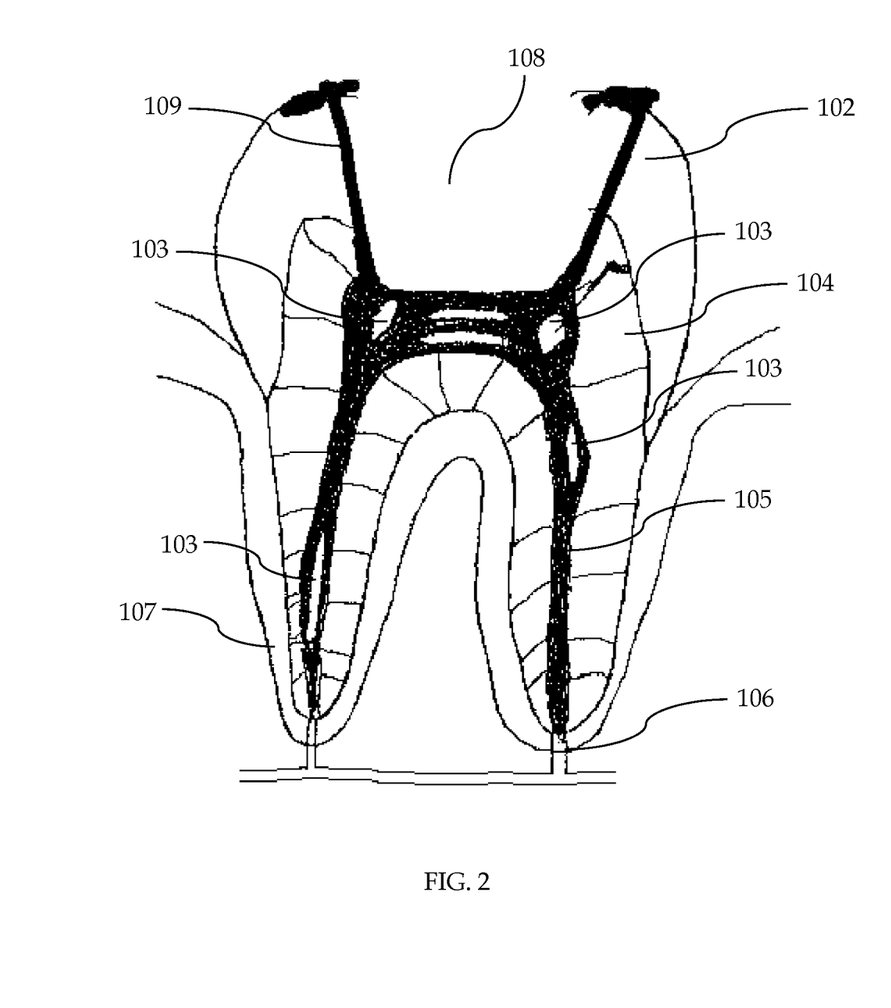
FIG. 2 illustrates the tooth of FIG. 1 at a stage of treatment showing access to the pulpal chamber in accordance with an embodiment of the present invention.

FIG. 2 depicts the tooth 100, during the root canal treatment, according to an embodiment of the present invention. The pulpal chamber is accessed, as shown in the figure. FIG. 2 further depicts access to the cavity 108, and access to cavity walls 109.

Figure 3:
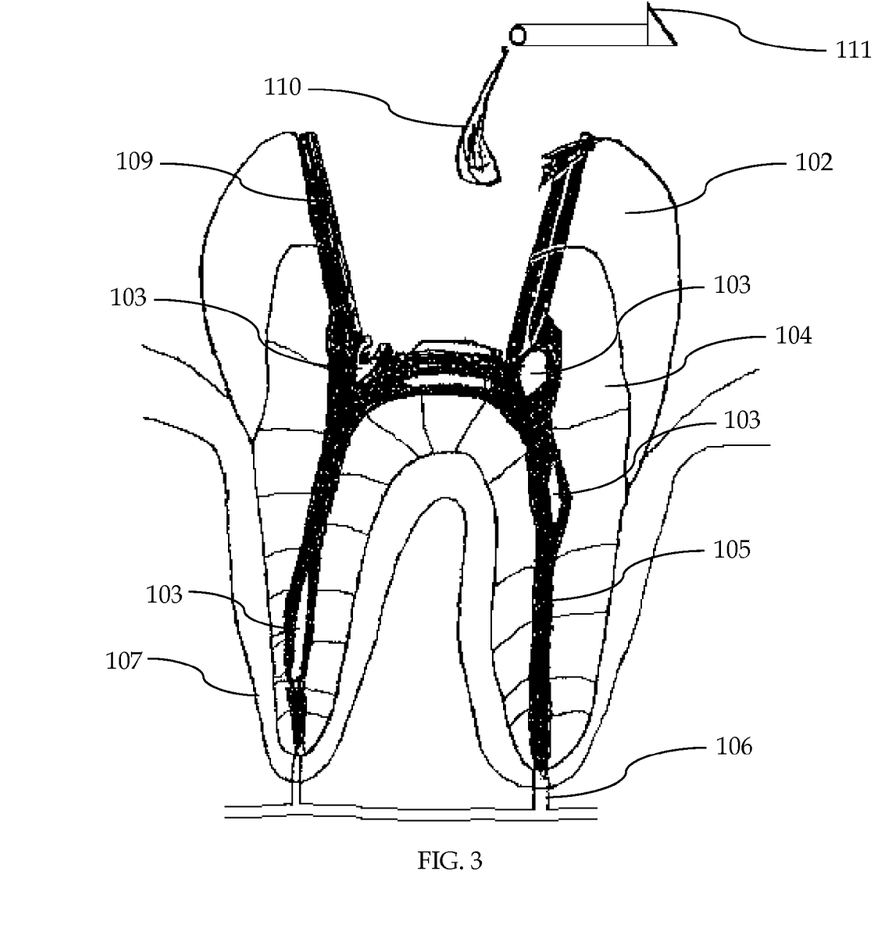
FIG. 3 illustrates the tooth of FIG. 1 at a further stage of treatment showing a composition being applied in accordance with an embodiment of the present invention.

FIG. 3 depicts introduction of a composition 110 into the cavity 108, according to an embodiment of the present invention. The composition is placed into the cavity 108 by using a disposable needle 111.

According to an embodiment of the present invention, the composition 110 is a chemical depilatory. The present invention utilizes the chemical depilatory as an endodontic intracanal medicament for irrigation, disinfection, and lubrication to provide anti-microbial properties and further facilitate removal of smear layer. In an embodiment of the present invention, the composition 110 breaks the disulfide bonds of pulpal tissue. The breakage of the disulfide bonds degrades structure of the pulpal tissue in order to remove tissue.

The chemical depilatories have been used for a wide variety of purposes. For example, chemical depilatories have been used for reducing microbial levels on the hide of an animal. Further, the chemical depilatories have been used in removal of hair from skin and outer extremities as from the arms, legs, face, and underarms. Furthermore, the chemical depilatories have been used to remove unwanted hairs from the external skin of both animals and humans.

Further, tissues of the pulp 105 and hair have a similar characteristic of containing disulfide bonds as both are derived from neural crest stem cells. The hair follicle bulge is derived from cranial neural crest, and similarly the dental pulp and periodontal ligament are derived from the neural crest. Since, the chemical depilatories has been used in hair, the present invention utilizes the chemical depilatories in endodontic usage as well.

According to an embodiment of the present invention, the composition 110 includes active ingredients of calcium hydroxide, sodium hydroxide, and potassium thioglycolate. In an embodiment of the present invention, the composition 110 further includes mineral oil, urea, cetearyl alcohol and ceteth-20 for contributing to ability of the composition 110 to produce desired results.

According to an embodiment of the present invention, the composition 110 is capable of dislodging calcifications that lie within root canal system by weakening attached connective tissue as well as removal of soft tissue from the cavity of a hard, bony tissue. In an embodiment of the present invention, the composition 110 provides a single endodontic irrigant composition that dissolves tissue, removes the smear layer, and includes antibacterial capability.

Further, in an embodiment of the present invention, the composition 110 (or chemical depilatory) may be used by a dental professional in an unprepared as well as prepared root canal system in order to facilitate the instrumentation of root canal walls and pulpal chamber by dislodging calcifications, removing pulpal tissue and debris.

The composition 110 may do multiple roles in the root canal treatment. For example, the composition 110 may act as an irrigant, disinfectant, chelation agent, conditioner, antimicrobial agent and lubricant for endodontic chemomechanical preparation of the root canal space, according to an embodiment of the present invention. The composition 110 includes calcium hydroxide, sodium hydroxide, and potassium thioglycolate in combination. Further, in an embodiment of the present invention, the composition 110 may include mineral oil, urea, cetearyl alcohol and ceteth-20 for use for irrigation, disinfection, lubrication, removing the smear layer, dissolving pupal tissue and as an anti-bacterial agent.

In an embodiment of the present invention, the composition 110 may be used in endodontic usages during intracanal instrumentation in order to break disulfide bonds present in pulpal tissue, to remove the smear layer, and to be effective against bacteria present in the root canal system. According to an embodiment, the composition 110 may be used as a single endodontic irrigant on unprepared as well as prepared tooth surfaces in order to dissolve tissue, remove the smear layer, and be effective against bacteria. The composition 110 may further provide for removal of soft tissue inside of a hard, bony cavity. Further, according to an embodiment of the present invention, the composition 110 may provide preparation of regeneration and formation of mineralized and soft tissue in a hard bony cavity (e.g., a human or animal). Furthermore, the composition 110 may be used in medicine, for example, in long bones and in preparing skeletons for museums, etc.

Figure 4:
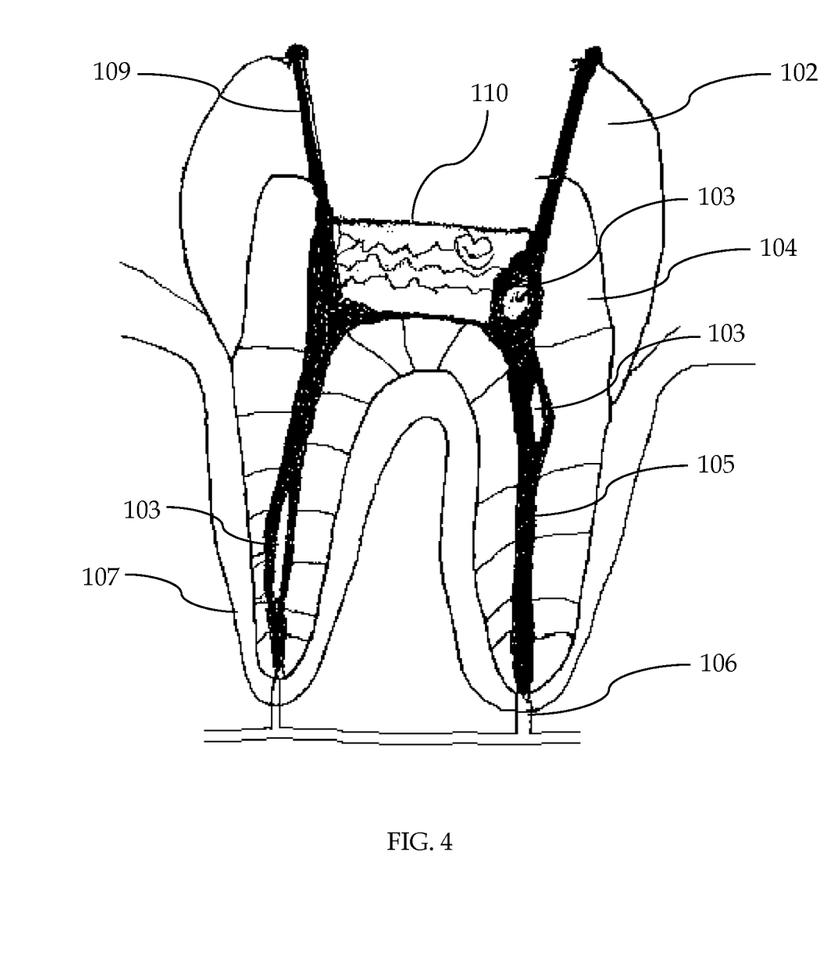
FIG. 4 illustrates the tooth of FIG. 1 at a further stage of treatment showing a composition accessing the cavity's floor in accordance with an embodiment of the present invention.

FIG. 4 depicts the composition 110 accessing the cavity's floor 108 as well as the cavity walls 109. The composition 110 provides removal of soft, connective tissue (i.e., pulp tissues) from within a hard tissue cavity (i.e., enamel and dentin) and hard bony cavities. In an embodiment of the present invention, the composition 110 is a chemical depilatory that removes soft tissue, necrotic tissue, debris, and calcified tissue from within the hard tissue cavity. In an embodiment of the present invention, the composition 110 functions as an intra-canal medicament with properties of an irrigant, disinfectant, lubricant, antimicrobial agent, debriding agent, and cleansing agent (as it is capable of removing the smear layer). The composition 110 is further capable for chemo-mechanical cleansing and enlarging of the root canal system. Furthermore, the composition 110 is also capable of bleaching teeth.

According to an embodiment of the present invention, the composition 110 includes active ingredients of calcium hydroxide, sodium hydroxide, and potassium thioglycolate, as discussed above.

In one embodiment of the present invention, calcium hydroxide (present in the composition 110) creates an alkaline environment so that endodontic pathogens are not able to survive. Further, in an embodiment of the present invention, sodium hydroxide (which is a strong base) is used in tissue digestion by bleaching. Further, the sodium hydroxide breaks down chemical bonds and further keeps the flesh intact.

Further, in an embodiment of the present invention, potassium thioglycolate (present in the composition 110) breaks down sulfur bonds present in keratin protein of pulp. Potassium thioglycolate reacts with the cystine present in the protein. The reaction is following: 2SH—CH2-COOH (thioglycolic acid)+R—S—S—R (cystine=disulfide bridge) →2R—SH+COOHCH2SSCH2COOH (dithiodiglycolic acid).

Further, in an embodiment of the present invention the composition 110 may include one or more of following constituents including, but not limited to, water, mineral oil, urea, cetearyl alcohol, D&C yellow No. 8, chromium hydroxide, theobroma cocoa seed butter, iron oxides, fragrances, and ceteareth-20. According to an embodiment of the present invention, the mineral oil may fill surface cracks. Those skilled in the art will appreciate that the surface cracks if not filled, may harbor bacteria. Further, the mineral oil may act as a lubricant. Further, according to an embodiment of the present invention, the urea may retain moisture, prevent skin infections, and treat inflammatory conditions in the skin.

Further, according to an embodiment of the present invention, the composition may include a coconut oil. The cetearyl alcohol can emulsify with ceterth-20 can to enhance viscosity of the lotion.

Figure 5:
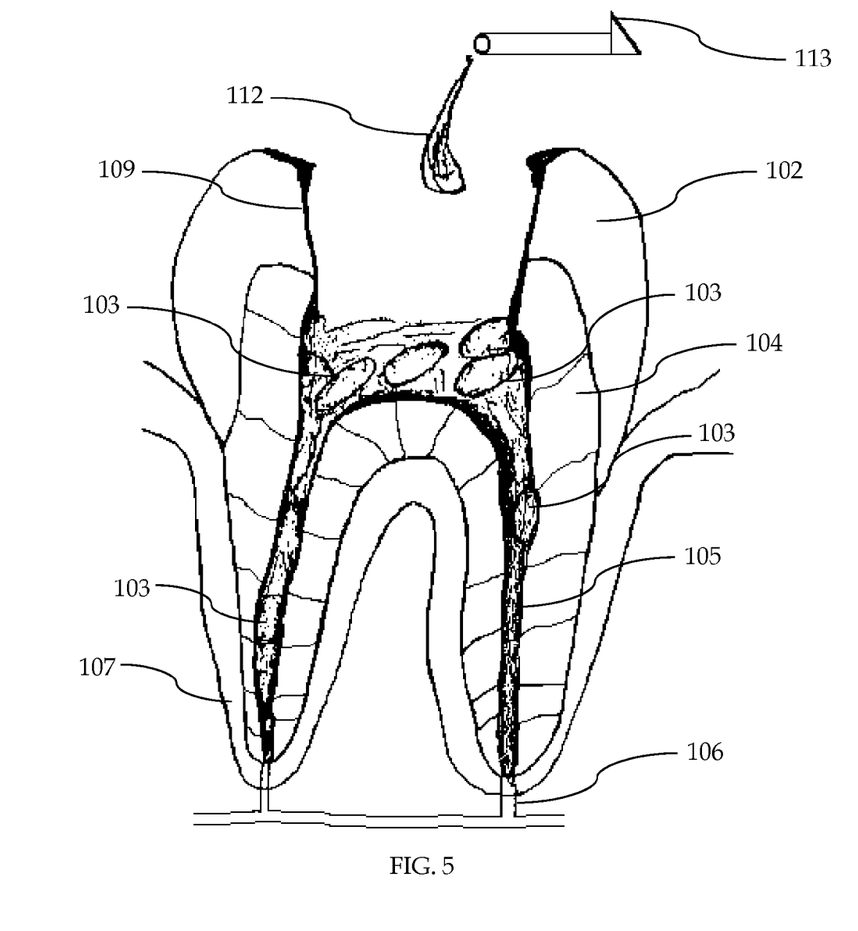
FIG. 5 illustrates the tooth of FIG. 1 at a further stage of treatment showing a rinsing solution in accordance with an embodiment of the present invention.

Once, the pulp has been cleaned out and root canal area disinfected with help of the composition, a rinsing solution may be introduced, as shown in FIG. 5.

Figure 6:
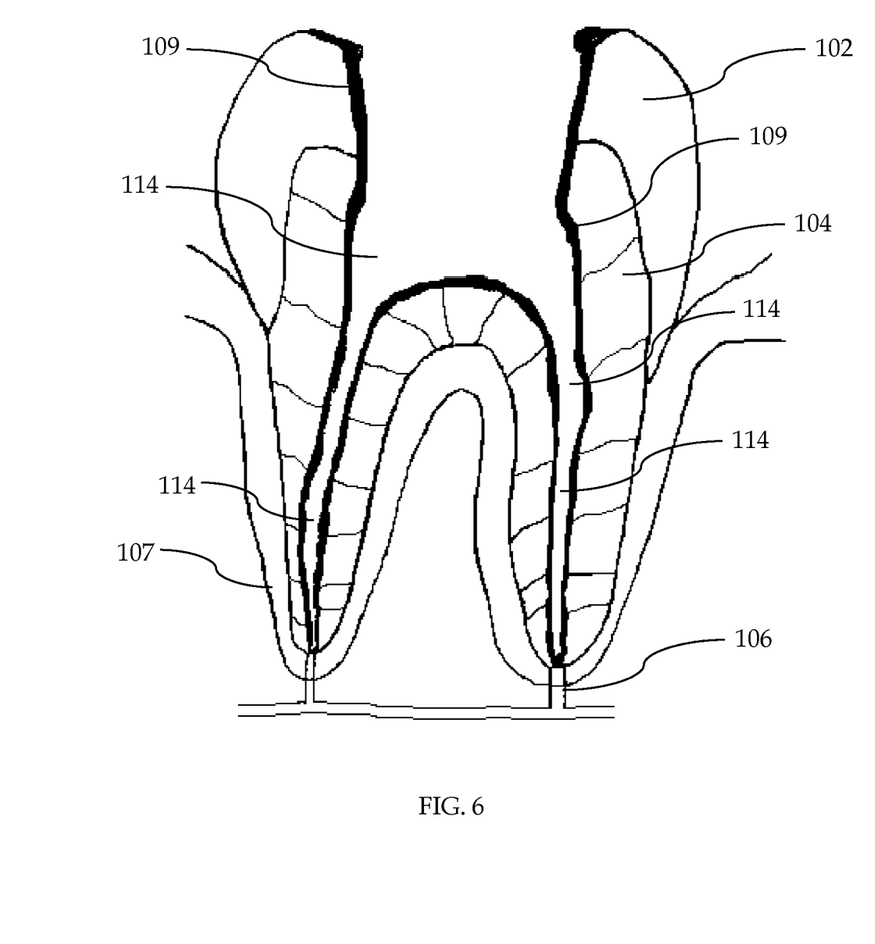
FIG. 6 illustrates the tooth of FIG. 1 at a further stage of treatment showing the tooth after rinsing and the empty root canal in accordance with an embodiment of the present invention.

FIG. 5 shows introduction of a rinsing solution 112 using a disposable needle 113 for applying the rinsing solution. FIG. 6 shows the tooth 100 after rinsing with an empty root canal system 114.

According to an embodiment of the present invention, the composition 110 (i.e., the chemical depilatory) breaks the disulfide bonds in the pulpal tissues. Therefore, any pulp stones attached to weakened pulpal tissues can also be removed. The breaking of bonds aids in the removal of unwanted pulpal tissue and debris. The composition 110 further lubricates, irrigates, disinfects, dissolves, cleanses and removes the smear layer. Further, the composition 110 (or the chemical depilatory) provides antimicrobial protection again infections.

The composition 110 includes chemicals (that breaks the disulfide bonds, e.g., calcium hydroxide, sodium hydroxide, and potassium thioglycolate) with other substances (that are needed to lubricate, dissolve, disinfect and remove pulpal debris, e.g., mineral oil, urea, cetearyl alcohol and ceteth-20). The disulfide bonds are present in myelinated sheath of nerves that enters the tooth via its apical opening. The composition 110 weakens portion of the myelinated sheath of an entering nerve within the root canal system, so that, it can be easily scraped off the inner root canal wall of the tooth. For example, the chemical depilatories removes the hair from the follicle by weakening it at the point that it emerges from the follicle, the present invention utilizes the chemical depilatories in weakening nerve's protection by breaking down the disulfide bond in the myelinated sheath that surrounds and protects the nerve.

Further, the composition 110 provides cleansing and debriding the pulp chamber and root canal space. The composition 110 further removes smear layer by breaking the disulfide bonds present in glycosaminoglycans (GAG), which is the matrix of the inorganic layer. Furthermore, the composition 110 provides dislodging pulpal calcifications by breaking bonds within the tissue that surrounds the calcification.

Hence, the composition 110 provides disinfecting, cleansing, irrigating and lubricating both prepared and unprepared tooth surfaces during dental procedures. The composition 110 may be used in endodontic during non-surgical root canal therapy during intra-canal chemo-mechanical preparation. Also, the composition 110 further may be used to remove the debris that is formed during dental procedure and dissolve proteins within the pulpal chamber.

Further, according to embodiment of the present invention, the composition 110 may be used for cleaning, irrigating, disinfecting, etc. of inside of any bony cavity (e.g., a hard bony cavity). For example, the composition may be used for intra-medullary reaming and irrigating (e.g., to be used before a rod in orthopedics), maceration (e.g., cleaning animal skulls & bones used of preserving them), preparing a bony surface for stem cells, for regeneration of new tissue, and for formation of mineralized tissue.

Further, the composition 110 may be used for preparing a bony surface for cellular differentiation, tissue formation, and tissue regeneration. Those skilled in the art will appreciate that for making regeneration of stem cells successful, the diseased or unwanted cells must be removed as they damage the underlying tissues' ability to generate on its own new cells. In an embodiment of the present invention, the composition 110 removes the diseased or unwanted cells, and provides a clean area for regeneration of stem cells.

Further, the composition 110 may assist a dentist to prepare the tooth surface to place stem cells inside the tooth for pulpal and tissue regeneration. The stem cells may be used within the pulpal chamber. For example, an embodiment of the present invention provides a root canal therapy whereby a root canal procedure will be cleaning the chamber/roots and then placing stem cells to re-grow pulpal, dentinal and mineralized tissue. Those skilled in the art will appreciate that this can only be performed if the composition 110 as described hereinabove is first used to clean the inside of the tooth 100, and failure to clean the inside of the tooth 100 sufficiently will not provide a clean enough surface for the placement of stem cells. The composition 110, provided by the present invention, provides cleaning of the inside of the tooth 100 and provides a clean surface for placement of stem cells. Furthermore, according to an embodiment of the present invention, the composition 110 may also provide bleaching of teeth.

Figure 7:
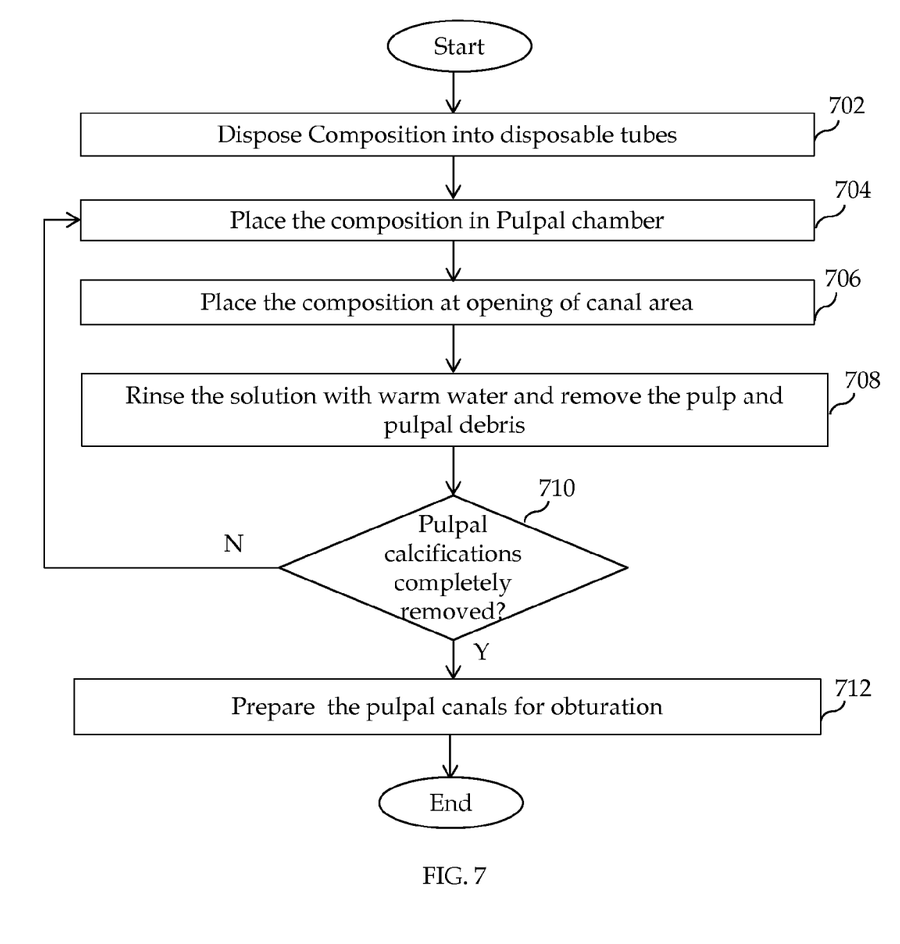
FIG. 7 is a flow chart depicting root canal treatment using a composition, in accordance with an embodiment of the present invention.

FIG. 7 is a flowchart of a method 700 for cleaning out pulp and disinfecting root canal area in a root canal treatment, according to an embodiment of the present invention. According to an embodiment of the present invention, the method 700 provides using a chemical depilatory as a composition in endodontic. The method 700 is effective due to disulfide bonds presence in pulpal tissue of tooth.

At step 702, a chemical depilatory composition is dispensed into disposal tubes. Further, disposal needles may be attached to the disposable tubes. According to an embodiment of the present invention, the composition may include calcium hydroxide, sodium hydroxide, and potassium thioglycolate. In one embodiment of the present invention, calcium hydroxide (present in the composition) creates an alkaline environment so that endodontic pathogens are not able to survive. Further, in an embodiment of the present invention, sodium hydroxide (which is a strong base) is used in tissue digestion by bleaching. Further, the sodium hydroxide breaks down chemical bonds and further keeps the flesh intact. Furthermore, in an embodiment of the present invention, potassium thioglycolate (present in the composition) breaks down sulfur bonds present in keratin protein of pulp.

In another embodiment of the present invention, the composition may further include mineral oil, urea, cetearyl alcohol, D&C yellow No. 8, chromium hydroxide, theobroma cocoa seed butter, iron oxides, fragrances, and ceteareth-20 to enhance its functioning, in addition to calcium hydroxide, sodium hydroxide, and potassium thioglycolate. According to an embodiment of the present invention, the mineral oil may fill surface cracks. Further, the mineral oil may act as a lubricant. Further, according to an embodiment of the present invention, the urea may retain moisture, prevent skin infections, and treat inflammatory conditions in the skin. Further, according to an embodiment of the present invention, the cetearyl alcohol can emulsify with ceterth-20 can to form cetereth-20 and enhances viscosity of the lotion. In an embodiment, the cetearyl alcohol may include a coconut oil.

At step 704, a few drops of the composition are placed in the pulpal chamber to wet the floor with the disposable needle. At step 706, the composition or solution is placed it at opening of the canal for going inside the canal with help of an endodontic file/reamer/instrument of choice, coat the 'file' with the solution and. The solution is left there for about 1-3 minutes.

At step 708, the composition or solution is rinsed with warm water. Further, in an embodiment, the solution may also be rinsed with warm sodium hypochloride. In another embodiment, the solution may also be rinsed with other commercial, conventional irrigants. Further, the pulp and pulpal debris is removed and irrigated out.

At step 710, it is determined whether the pulpal calcifications or infected/damaged area of tooth has been completely removed and dislodged, and the canal area has been completely disinfected. In case, there are still some tissues of pulp remaining or infection remaining, flow of the method 700 returns to 702. Otherwise, the method 700 proceeds towards 712, wherein the pulpal canal is prepared for obturation. In an embodiment, a mechanical instrument procedure may be carried out for obturating the pulpal canal. At 714, the method 700 concludes.

Test Results

Test results will now be provided here to illustrate the above principles. The following example illustrates working of the present invention in accordance with an embodiment of the present invention. A person of ordinary skilled in the art will appreciate the present invention may be performed for any medical use and is not limited to any particular medical application.

Testing of the present invention's anti-microbial activity was done in an independent laboratory in accordance with the USFDA Regulations 21 CFR Part 58. The testing of the present invention was done under the supervision of a quality assurance supervisor and a study director. The study was done at an off-site laboratory that performed the tests under protocol that includes reproducibility of test results and details to allow for inspection. The laboratory keeps all the documentation and details on file.

The testing of the test organism was done with contact time of 5 minutes, 15 minutes and 30 minutes. The time intervals were chosen so as to correspond to times that practitioners use in clinical practice. The maximum time was chosen as 30 minutes, since actual treatment time is approximately equal to 30 minutes. Keeping patient's mouth open for 30 minutes maximum for a procedure is reasonable. Tome required for instrumentation for an endodontic procedure is estimated around 5 minutes. Fifteen minutes may be needed, when the practitioner uses the instrument before an obturation procedure in a second visit when two visits are needed for non-surgical root canal treatment. Recovery times were tested for bacteria using 2-5 days times and *C. albicans* with 2-5 days intervals. Recovery values are the colonies forming abilities.

The plate counts are based on colony formation units (CFU)/plate for both bacteria and yeast. For bacteria and yeast, the 25-250 CFU/plate are statistically accurate range. For mold, 8-80 CFU/plate is statistically accurate range. Soybean Casein Digest Agar was used as the medium for plates of the test organism of *S. mutans* and *E. faecalis*. Sabouraud Dextrose Agar was used for *C. albicans*. All plates were handled under laboratory conditions with their controls.

The test micro-organisms (i.e., *E. faecalis, C. albicans,* and *S. mutans*) were picked because they are the prevalent organisms in Endodontic infections. Endodontic infections are mixed microorganisms or flora. *Candida albicans, Streptococcus mutans* and *Enterococci faecalis* are the microorganisms that have a major presence in the endodontic lesion, which all need to be eradicated. *Candida albicans* are typically opportunistic infections in humans. *Candida albicans* are yeasts that are in infections of root canals and cause oral candidiasis and are prevalent in HIV cases. The treatment of candidosis is by the use of anti-fungal treatment and not by antibiotics. *Streptococcus mutans* have a large presence in dental caries and has the ability to dematerialize enamel by its ability to reach the critical pH that is needed. Furthermore, *S. mutans* has a significant presence in root canal infections, since it has the ability to survive levels of oxygen tension and absence of essential nutrients. *S. mutans* can maintain microbial growth and continue acid production at low pH values. *Enterococci faecalis* is found most commonly in persistent radiographic lesions after root canal treatment. Due to the prevalence of *E. faecalis* in persistent endodontic infections, it is essential that the main persistent etiologic agent is eradicated during root canal instrumentation. Therefore, complete removal of irritants from the root canal system is best and most effective way to eradicate root canal infections.

The test results describe procedure for evaluation of products for anti-microbial activity against selected organisms at representative contact times. Products are evaluated in a liquid matrix. The test organisms and contact times are chosen by sponsor. This is a quantitative test that allows the determination of the amount of organism reduction at predetermined intervals. All test method acceptance criteria were met. The acceptance criteria were that negative controls should be negative for growth, positive controls should be positive for growth, and neutralization should be confirmed at ~70% Specific criteria for pass/fail of the test article must be determined by the sponsor.

Inoculum Preparation: Plates of Soybean Casein Digest Agar (SCDA) media were inoculated with stock cultures of the test organisms S. mutans and E. faecalis and incubated at 30-35° C. for 18-48 hours. Plates of Sabouraud Dextrose Agar (SDEX) media were inoculated with stock cultures of the test organism C. albicans and incubated at 20-25° C. for 44-52 hours. Growth was harvested from the surface using a sterile bent glass rod and Physiological Saline Solution 0.9% (PHSS).

Where necessary, culture suspensions were adjusted for the test procedure with PHSS to approximately (~) $10^8$ CFU/ml using visual turbidity.

Test Article Preparation: Test articles were prepared according to the product label or sponsor instructions and were tested without any additional manipulation or dilution.

Neutralization: A 0.1 ml aliquot of the test article was mixed with 9.9 ml Dey-Engley Neutralizer Broth (DEYE). An additional tube of 10 mL of DEYE was prepared as a titer control. The tubes were inoculated with 0.1 ml of a test organism suspension diluted to approximately 10,000 CFU/mL, then mixed thoroughly. Aliquots from each tube were plated in triplicate onto SCDA and incubated at 30-35° C. for 2-5 days for S mutans and E. faecalis. Aliquots from each tube were plated in triplicate onto SDEX and incubated at 20-25° C. for 2-5 days for C. albicans.

Controls: Positive control tubes containing 10 mL PHSS were prepared. A 0.1 mL aliquot of the test organism was added to each tube. The positive control was assayed at 0 hour and the longest tested time point. The negative control consisted of plating sterile aliquots of applicable liquid media in triplicate and incubating as described in the test procedure.

Test Procedure: Tubes containing 10 mL of each test article were prepared and inoculated with 0.1 mL of the test organism to yield ~$10^6$ CFU/mL. The test articles were mixed thoroughly.

At 5 minutes, 15 minutes and 30 minutes of exposure, 1.0 mL aliquots of the test suspension were removed and added to 9 mL of neutralizer and serially diluted to produce a 1:100 dilution of test suspension to neutralizer. The tubes were mixed thoroughly. Serial dilutions were made in the appropriate neutralizer and assayed using a standard spread plate method.

All plating was performed in triplicate. Bacterial test articles were plated onto SCDA and incubated at 30-35° C. for 2-5 days. Yeast test articles were plated onto SDEX and incubated at 20-25° C. for 2-5 days.

Quantitative analysis was used to study the anti-microbial activity of the present invention. The following formulas were used by the independent laboratory in preparing their report of the effectiveness of the present invention.

Calculations: The log reduction values were calculated using the following formula:

$$\log \text{reduction} = \log_{10} U - \log_{10} C$$

Wherein, U=Average positive control titer, C=Average recovered counts

The percent reduction values were calculated using the following formula:

$$\% \text{ Reduction} = [1 - 1/10^{(\log \text{ reduction})}] \times 100$$

The percent neutralization is obtained according to the following equation:

$$\% \text{ Neutralization} = [(\text{Average Sample Count/Plate})/(\text{Average Control Count/Plate})] \times 100$$

Test Article—*Enterococcus faecalis*

| Identification | Exposure Intervals | Average Control Titer (CFU/ml) | Average Test Article Titer (CFU/ml) | Percent Reduction (%) | $\log_{10}$ Reduction |
|---|---|---|---|---|---|
| Control | 30 minutes | $1.1 \times 10^7$ | $1.0 \times 10^7$ | 7 | 0.03 |
| | 5 minutes | | $<2.0 \times 10^2$ | >99.9982 | >4.74 |
| Sample 1 | 15 minutes | $1.1 \times 10^7$ | $<2.0 \times 10^2$ | >99.9982 | >4.74 |
| | 30 minutes | | $<2.0 \times 10^2$ | >99.9982 | >4.74 |

Test Article—*Candida albicans*

| Identification | Exposure Intervals | Average Control Titer (CFU/ml) | Average Test Article Titer (CFU/ml) | Percent Reduction (%) | $\log_{10}$ Reduction |
|---|---|---|---|---|---|
| Control | 30 minutes | $8.5 \times 10^6$ | $1.0 \times 10^7$ | −32 | −0.12 |
| | 5 minutes | | $<2.0 \times 10^2$ | >99.9976 | >4.63 |
| Sample 1 | 15 minutes | $8.5 \times 10^6$ | $<2.0 \times 10^2$ | >99.9976 | >4.63 |
| | 30 minutes | | $<2.0 \times 10^2$ | >99.9976 | >4.63 |

Test Article—*Streptococcus mutans*

| Identification | Exposure Intervals | Average Control Titer (CFU/ml) | Average Test Article Titer (CFU/ml) | Percent Reduction (%) | $\log_{10}$ Reduction |
|---|---|---|---|---|---|
| Control | 30 minutes | $4.1 \times 10^7$ | $4.5 \times 10^7$ | −11 | −0.05 |
| | 5 minutes | | $<2.0 \times 10^2$ | >99.99951 | >5.31 |
| Sample 1 | 15 minutes | $4.1 \times 10^7$ | $<2.0 \times 10^2$ | >99.99951 | >5.31 |
| | 30 minutes | | $<2.0 \times 10^2$ | >99.99951 | >5.31 |

Neutralization

| Organism | Average control counts (CFU) | Average test article counts (CFU) | Percent Neutralization (%) |
|---|---|---|---|
| E. faecalis | 40 | 41 | 103 |
| C. albicans | 36 | 46 | 128 |
| S. mutans | ~7 | ~9 | ~129 |

The qualitative analysis, given here, confirms that the present invention is very useful and successful in its ability to disinfect the pulpal chamber from the test microorganisms (i.e., E. faecalis, C. albicans, and S. mutans). The qualitative analysis for all of the three test microorganisms at all of the time intervals had a greater than 99.9951% reduction of test microorganism. Neutralization of the microorganisms was successful because all of the percentage for neutralization was over 70% which was needed for confirmation. Furthermore, in the recovery testing, there were no colonies forming units in any of the plates with any of the test microorganisms. Therefore, the microorganisms did not regenerate and did not reappear. The lack of the microorganisms present in the recovery results proves that the present invention is able to eradicate all the test materials/microorganisms during the instrumentation.

Above test results prove that the composition, as provided by the present invention, provides anti-microbial activity against above organisms (i.e., *E. faecalis, C. albicans*, and *S. mutans*). Further, the tests show that the composition (i.e., chemical depilatory) provides unexpected results by proving useful in endodontic usages and that also, in a very short time.

The exemplary systems and methods of this present invention have been described in relation to a root canal treatment and removal of tissue from within a hard bony structure. However, to avoid unnecessarily obscuring the present invention, the preceding description omits a number of known structures and devices. This omission is not to be construed as a limitation of the scope of the claimed invention. Specific details are set forth to provide an understanding of the present invention. It should however be appreciated that the present invention may be practiced in a variety of ways beyond the specific detail set forth herein.

Also, while the flowcharts have been discussed and illustrated in relation to a particular sequence of events, it should be appreciated that changes, additions, and omissions to this sequence can occur without materially affecting the operation of the present invention.

A number of variations and modifications of the present invention can be used. It would be possible to provide for some features of the present invention without providing others.

While the foregoing is directed to embodiments of the present invention, other and further embodiments of the present invention may be devised without departing from the basic scope thereof. It is understood that various embodiments described herein may be utilized in combination with any other embodiment described, without departing from the scope contained herein. Further, the foregoing description is not intended to be exhaustive or to limit the present invention to the precise form disclosed. Modifications and variations are possible in light of the above teachings or may be acquired from practice of the present invention.

Certain exemplary embodiments may be identified by use of an open-ended list that includes wording to indicate the list items are representative of the embodiments and the list is not intended to represent a closed list exclusive of further embodiments. Such wording may include "e.g.," "etc.," "such as," "for example," "and so forth," "and the like," etc., and other wording as will be apparent from the surrounding context.

No element, act, or instruction used in the description of the present application should be construed as critical or essential to the present invention unless explicitly described as such. Also, as used herein, the article "a" is intended to include one or more items. Where only one item is intended, the term "one" or similar language is used. Further, the terms any of followed by a listing of a plurality of items and/or a plurality of categories of items, as used herein, are intended to include "any of," "any combination of," "any multiple of," and/or "any combination of multiples" of the items and/or the categories of items, individually or in conjunction with other items and/or other categories of items.

The present invention, in various embodiments, configurations, and aspects, includes components, methods, processes, systems and/or apparatus substantially as depicted and described herein, including various embodiments, subcombinations, and subsets thereof. Those of skill in the art will understand how to make and use the present invention after understanding the present disclosure. The present invention, in various embodiments, configurations, and aspects, includes providing devices and processes in the absence of items not depicted and/or described herein or in various embodiments, configurations, or aspects hereof, including in the absence of such items as may have been used in previous devices or processes, e.g., for improving performance, achieving ease and/or reducing cost of implementation.

The foregoing discussion of the present invention has been presented for purposes of illustration and description. The foregoing is not intended to limit the present invention to the form or forms disclosed herein. In the foregoing Detailed Description for example, various features of the present invention are grouped together in one or more embodiments, configurations, or aspects for the purpose of streamlining the disclosure. The features of the embodiments, configurations, or aspects of the present invention may be combined in alternate embodiments, configurations, or aspects other than those discussed above. This method of disclosure is not to be interpreted as reflecting an intention that the claimed invention requires more features than are expressly recited in each claim. Rather, as the following claims reflect, inventive aspects lie in less than all features of a single foregoing disclosed embodiment, configuration, or aspect. Thus, the following claims are hereby incorporated into this Detailed Description, with each claim standing on its own as a separate preferred embodiment of the present invention.

Moreover, though the description of the present invention has included description of one or more embodiments, configurations, or aspects and certain variations and modifications, other variations, combinations, and modifications are within the scope of the present invention, e.g., as may be within the skill and knowledge of those in the art, after understanding the present disclosure. It is intended to obtain rights which include alternative embodiments, configurations, or aspects to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A composition, for use in endodontic irrigation, tissue dissolution, disinfection, and lubrication, and eradicating microorganisms from dentinal and enamel surfaces of a tooth, inorganic surfaces, bony surfaces and connective tissues, and for facilitating chemo-mechanical debridement of root canal systems, wherein the composition consists of: calcium hydroxide, sodium hydroxide, potassium thioglycolate, water, mineral oil, urea, cetearyl alcohol, D & C yellow No. 8, chromium hydroxide, theobroma cocoa seed butter, iron oxide, a fragrance, ceteareth-20, and coconut oil; and wherein the mineral oil is included in the composition to fill surface cracks, the urea is included in the composition to retain moisture, prevent infections and inflammation, and the cetearyl alcohol is included in the composition to enhance viscosity.

2. The composition of claim 1, wherein the composition is used in a root canal treatment and inside a hard bony cavity.

3. The composition of claim 1, wherein the calcium hydroxide creates an alkaline environment.

4. The composition of claim 1, wherein the sodium hydroxide breaks down chemical bonds.

5. The composition of claim 1, wherein the potassium thioglycolate breaks down disulphide bonds in pulpal tissues of pulp of a tooth.

6. The composition of claim 5, wherein the composition degrades structure of pulpal tissue for removing the pulpal tissues and soft tissue within a hard bony cavity.

7. The composition of claim 1, wherein the composition is used in long bones and in preparing skeletons for museums.

8. The composition of claim 1, wherein the composition is effective on prepared surfaces, unprepared surfaces, and in removing smear layer on dental walls.

9. The composition of claim 1, wherein the composition is capable of dislodging calcifications that lie within root canal system and in hard bony cavities by weakening attached connective tissue as well as removal of soft tissue from pulp of a tooth.

* * * * *